(12) United States Patent
Nord et al.

(10) Patent No.: US 8,075,550 B2
(45) Date of Patent: Dec. 13, 2011

(54) PIERCING MEMBER PROTECTION DEVICE

(75) Inventors: Lars Nord, Gothenburg (SE); Petri Horppu, Stockholm (SE)

(73) Assignee: Carmel Pharma AB, Göteborg (SE)

( * ) Notice: Subject to any disclaimer, the term of this patent is extended or adjusted under 35 U.S.C. 154(b) by 199 days.

(21) Appl. No.: 12/166,155

(22) Filed: Jul. 1, 2008

(65) Prior Publication Data

US 2010/0004602 A1   Jan. 7, 2010

(51) Int. Cl.
*A61M 25/16* (2006.01)
*A61M 5/32* (2006.01)

(52) U.S. Cl. ........ 604/533; 604/534; 604/535; 604/539; 604/198

(58) Field of Classification Search .................. 604/110, 604/187, 192, 198, 196, 533–535, 538, 539; 175/19; 141/329
See application file for complete search history.

(56) References Cited

U.S. PATENT DOCUMENTS

| | | |
|---|---|---|
| 1,844,342 A | 2/1932 | Berman |
| 2,010,417 A | 8/1935 | Schwab |
| 2,697,438 A | 12/1954 | Hickey |
| 2,717,599 A | 9/1955 | Huber |
| 3,064,651 A | 11/1962 | Henderson |
| 3,071,135 A | 1/1963 | Baldwin et al. |
| 3,308,822 A | 3/1967 | DeLuca |
| 3,316,908 A | 5/1967 | Burke |
| 3,340,671 A | 9/1967 | Loo |
| 3,390,677 A | 7/1968 | Razimbaud |
| 3,448,740 A | 6/1969 | Figge |
| 3,542,240 A | 11/1970 | Solowey |
| 3,783,895 A | 1/1974 | Weichselbaum |
| 3,788,320 A | 1/1974 | Dye |
| 3,822,700 A | 7/1974 | Pennington |
| 3,938,520 A | 2/1976 | Scislowicz et al. |
| 3,976,073 A | 8/1976 | Quick et al. |
| 4,096,860 A | 6/1978 | McLaughlin |

(Continued)

FOREIGN PATENT DOCUMENTS

AU          200112863          5/2003

(Continued)

OTHER PUBLICATIONS

Taiwan Search Report for Taiwan Patent Application 092106323 dated Mar. 21, 2003 (4 pages).

(Continued)

*Primary Examiner* — Kevin C Sirmons
*Assistant Examiner* — Bradley Thomas, Jr.
(74) *Attorney, Agent, or Firm* — Fish & Richardson P.C.

(57) ABSTRACT

The present invention relates to a piercing member protection device (9) which comprises a first, a second and a third cylindrical member (100, 200, 300). The first cylindrical member (100) is at least partly encompassed by the second cylindrical member (200), and the second cylindrical member (200) is at least partly encompassed by the third cylindrical member (300). The third cylindrical member (300) comprises a piercing member (400) having a piercing tip (401). A first locking arrangement (250) is arranged to enable or prevent the turning of the first and third cylindrical member, with respect to the second cylindrical member, while a second locking arrangement (350) is arranged to enable or prevent movement of the piercing member (400) along the longitudinal center axis A, so as to expose the piercing tip (401) of the piercing member (400). The piercing member protection device (9) provides a safe device which reduces the risk of accidental exposure of the piercing tip (401) and contamination for a user.

19 Claims, 7 Drawing Sheets

U.S. PATENT DOCUMENTS

| | | |
|---|---|---|
| 4,296,786 A | 10/1981 | Brignola |
| D270,568 S | 9/1983 | Armstrong |
| 4,490,139 A | 12/1984 | Huizenga et al. |
| 4,516,967 A | 5/1985 | Kopfer |
| 4,564,054 A | 1/1986 | Gustavsson |
| 4,573,967 A | 3/1986 | Hargrove et al. |
| 4,576,211 A | 3/1986 | Valentini et al. |
| 4,581,016 A | 4/1986 | Gettig |
| 4,582,223 A | 4/1986 | Kobe |
| 4,588,403 A | 5/1986 | Weiss et al. |
| 4,600,040 A | 7/1986 | Naslund |
| 4,623,343 A | 11/1986 | Thompson |
| 4,629,455 A | 12/1986 | Kanno |
| 4,632,673 A | 12/1986 | Tiitola et al. |
| 4,636,204 A | 1/1987 | Christopherson et al. |
| 4,673,400 A | 6/1987 | Martin |
| 4,673,404 A | 6/1987 | Gustavsson |
| 4,737,150 A | 4/1988 | Baeumle et al. |
| 4,752,287 A | 6/1988 | Kurtz et al. |
| 4,759,756 A | 7/1988 | Forman et al. |
| 4,768,568 A | 9/1988 | Fournier et al. |
| 4,792,329 A | 12/1988 | Schreuder |
| 4,804,015 A | 2/1989 | Albinsson |
| 4,822,340 A | 4/1989 | Kamstra |
| 4,826,492 A | 5/1989 | Magasi |
| 4,834,717 A | 5/1989 | Haber et al. |
| 4,842,585 A | 6/1989 | Witt |
| 4,850,978 A | 7/1989 | Dudar et al. |
| 4,864,717 A | 9/1989 | Baus, Jr. |
| 4,872,494 A | 10/1989 | Coccia |
| 4,878,897 A | 11/1989 | Katzin |
| 4,889,529 A | 12/1989 | Haindl |
| 4,898,209 A | 2/1990 | Zbed |
| 4,909,290 A | 3/1990 | Coccia |
| 4,932,937 A | 6/1990 | Gustavsson et al. |
| 4,944,736 A | 7/1990 | Holtz |
| 4,964,855 A * | 10/1990 | Todd et al. ............ 604/533 |
| 4,982,769 A | 1/1991 | Fournier et al. |
| 4,994,048 A | 2/1991 | Metzger |
| 4,997,083 A | 3/1991 | Loretti et al. |
| 5,017,186 A | 5/1991 | Arnold |
| 5,041,105 A | 8/1991 | D'Alo et al. |
| 5,061,264 A | 10/1991 | Scarrow |
| 5,071,413 A | 12/1991 | Utterberg |
| 5,122,116 A | 6/1992 | Kriesel et al. |
| 5,122,123 A | 6/1992 | Vaillancourt |
| 5,137,524 A | 8/1992 | Lynn et al. |
| 5,158,554 A | 10/1992 | Jepson et al. |
| 5,176,673 A | 1/1993 | Marrucchi |
| 5,199,947 A | 4/1993 | Lopez et al. |
| 5,201,725 A | 4/1993 | Kling |
| 5,207,658 A | 5/1993 | Rosen et al. |
| 5,232,109 A | 8/1993 | Tirrell et al. |
| 5,254,097 A | 10/1993 | Schock et al. |
| 5,279,576 A | 1/1994 | Loo et al. |
| 5,279,583 A | 1/1994 | Shober, Jr. et al. |
| 5,279,605 A | 1/1994 | Karrasch et al. |
| 5,308,347 A | 5/1994 | Sunago et al. |
| 5,312,366 A | 5/1994 | Vaillancourt |
| 5,328,480 A | 7/1994 | Melker et al. |
| 5,334,163 A | 8/1994 | Sinnett |
| 5,356,406 A | 10/1994 | Schraga |
| 5,385,545 A | 1/1995 | Kriesel et al. |
| 5,385,547 A | 1/1995 | Wong et al. |
| 5,389,085 A | 2/1995 | D'Alessio et al. |
| 5,405,326 A | 4/1995 | Haber et al. |
| 5,445,630 A | 8/1995 | Richmond |
| 5,447,501 A * | 9/1995 | Karlsson et al. ............ 604/198 |
| 5,456,675 A | 10/1995 | Wolbring et al. |
| 5,470,522 A | 11/1995 | Thome et al. |
| 5,478,328 A | 12/1995 | Silverman et al. |
| 5,478,337 A | 12/1995 | Okamoto et al. |
| 5,492,531 A | 2/1996 | Post et al. |
| 5,514,117 A | 5/1996 | Lynn |
| 5,515,871 A | 5/1996 | Bittner et al. |
| 5,536,259 A | 7/1996 | Utterberg |
| 5,575,780 A | 11/1996 | Saito |
| 5,593,028 A | 1/1997 | Haber et al. |
| 5,613,954 A | 3/1997 | Nelson et al. |
| 5,632,735 A | 5/1997 | Wyatt et al. |
| 5,647,845 A | 7/1997 | Haber et al. |
| 5,685,866 A | 11/1997 | Lopez |
| 5,752,942 A | 5/1998 | Doyle et al. |
| 5,766,147 A | 6/1998 | Sancoff et al. |
| 5,766,211 A | 6/1998 | Wood et al. |
| 5,782,872 A | 7/1998 | Muller |
| 5,795,336 A | 8/1998 | Romano et al. |
| 5,817,083 A | 10/1998 | Shemesh et al. |
| 5,820,609 A | 10/1998 | Saito |
| 5,827,262 A | 10/1998 | Neftel et al. |
| 5,837,262 A | 11/1998 | Golubev et al. |
| 5,875,931 A | 3/1999 | Py |
| 5,879,345 A | 3/1999 | Aneas |
| 5,897,526 A | 4/1999 | Vaillancourt |
| 5,934,510 A | 8/1999 | Anderson |
| 5,984,899 A | 11/1999 | D'Alessio et al. |
| 6,063,068 A | 5/2000 | Fowles et al. |
| D427,308 S | 6/2000 | Zinger |
| 6,070,623 A | 6/2000 | Aneas |
| 6,071,270 A | 6/2000 | Fowles et al. |
| 6,090,091 A | 7/2000 | Fowles et al. |
| 6,113,068 A | 9/2000 | Ryan |
| 6,113,583 A | 9/2000 | Fowles et al. |
| 6,142,446 A | 11/2000 | Leinsing |
| 6,146,362 A | 11/2000 | Turnbull et al. |
| 6,209,738 B1 | 4/2001 | Jansen et al. |
| 6,221,065 B1 | 4/2001 | Davis |
| 6,245,056 B1 | 6/2001 | Walker et al. |
| D445,501 S | 7/2001 | Niedospial, Jr. |
| 6,253,804 B1 | 7/2001 | Safabash |
| 6,258,078 B1 | 7/2001 | Thilly |
| 6,387,074 B1 | 5/2002 | Horppu et al. |
| 6,453,956 B2 | 9/2002 | Safabash |
| 6,471,674 B1 | 10/2002 | Emig et al. |
| 6,517,523 B1 | 2/2003 | Kaneko et al. |
| 6,537,263 B1 | 3/2003 | Aneas |
| 6,571,837 B2 | 6/2003 | Jansen et al. |
| 6,591,876 B2 | 7/2003 | Safabash |
| 6,644,367 B1 | 11/2003 | Savage et al. |
| 6,685,692 B2 | 2/2004 | Fathallah |
| 6,715,520 B2 | 4/2004 | Andreasson et al. |
| 6,761,286 B2 | 7/2004 | Py et al. |
| D495,416 S | 8/2004 | Dimeo et al. |
| 6,786,244 B1 | 9/2004 | Jones |
| D506,256 S | 6/2005 | Miyoshi et al. |
| 6,960,194 B2 * | 11/2005 | Hommann et al. ............ 604/198 |
| 7,000,806 B2 | 2/2006 | Py et al. |
| 7,080,672 B2 | 7/2006 | Fournier et al. |
| 7,297,140 B2 | 11/2007 | Orlu et al. |
| D570,477 S | 6/2008 | Gallogly et al. |
| D572,820 S | 7/2008 | Gallogly et al. |
| D577,438 S | 9/2008 | Gallogly et al. |
| D577,822 S | 9/2008 | Gallogly et al. |
| D582,033 S | 12/2008 | Baxter et al. |
| D605,755 S | 12/2009 | Baxter et al. |
| 7,703,486 B2 | 4/2010 | Costanzo |
| D616,984 S | 6/2010 | Gilboa |
| 7,744,581 B2 | 6/2010 | Wallen et al. |
| 2001/0021825 A1 | 9/2001 | Becker et al. |
| 2001/0025671 A1 | 10/2001 | Safabash |
| 2002/0002352 A1 | 1/2002 | Becker et al. |
| 2002/0082586 A1 | 6/2002 | Finley et al. |
| 2002/0127150 A1 | 9/2002 | Sasso |
| 2002/0177819 A1 | 11/2002 | Barker et al. |
| 2003/0010717 A1 | 1/2003 | Brugger et al. |
| 2003/0070726 A1 | 4/2003 | Andreasson et al. |
| 2003/0106610 A1 | 6/2003 | Roos et al. |
| 2003/0107628 A1 | 6/2003 | Fowles et al. |
| 2003/0199846 A1 | 10/2003 | Fowles et al. |
| 2003/0233083 A1 | 12/2003 | Houwaert et al. |
| 2004/0116858 A1 | 6/2004 | Heinz et al. |
| 2004/0199139 A1 | 10/2004 | Fowles et al. |
| 2004/0215147 A1 | 10/2004 | Wessman et al. |
| 2005/0215977 A1 | 9/2005 | Uschold |
| 2006/0025747 A1 | 2/2006 | Sullivan et al. |
| 2006/0106360 A1 | 5/2006 | Wong |
| 2006/0111667 A1 | 5/2006 | Matsuura et al. |

| | | | | | |
|---|---|---|---|---|---|
| 2006/0157984 A1 | 7/2006 | Rome et al. | JP | 49-12690 | 5/1972 |
| 2006/0186045 A1 | 8/2006 | Jensen et al. | JP | 288664 | 7/1990 |
| 2007/0021725 A1 | 1/2007 | Villette | JP | 3030963 | 8/1996 |
| 2007/0060841 A1 | 3/2007 | Henshaw | JP | 2000167022 | 6/2000 |
| 2007/0088313 A1 | 4/2007 | Zinger et al. | JP | 2001505092 | 4/2001 |
| 2007/0106244 A1 | 5/2007 | Mosler et al. | JP | 2001293085 | 10/2001 |
| 2007/0179441 A1* | 8/2007 | Chevallier ............... 604/110 | TW | 482670 | 4/2002 |
| 2007/0270759 A1* | 11/2007 | Pessin ..................... 604/192 | WO | WO 84/04672 | 12/1984 |
| 2007/0270778 A9 | 11/2007 | Zinger et al. | WO | WO 84/04673 | 12/1984 |
| 2008/0045919 A1 | 2/2008 | Jakob et al. | WO | WO 90/03536 | 4/1990 |
| 2008/0103453 A1* | 5/2008 | Liversidge .............. 604/187 | WO | WO 98/19724 | 5/1998 |
| 2008/0103485 A1 | 5/2008 | Kruger | WO | WO 99/27886 | 6/1999 |
| 2008/0172039 A1 | 7/2008 | Raines | WO | WO 99/62578 | 12/1999 |
| 2008/0223484 A1 | 9/2008 | Horppu | WO | WO 00/05292 | 2/2000 |
| 2008/0277021 A1 | 11/2008 | Horppu et al. | WO | WO 00/35517 | 6/2000 |
| 2008/0287920 A1 | 11/2008 | Fangrow et al. | WO | WO 01/80928 | 11/2001 |
| 2008/0312634 A1 | 12/2008 | Helmerson et al. | WO | WO 02/02048 | 1/2002 |
| 2009/0254042 A1* | 10/2009 | Gratwohl et al. ........... 604/198 | WO | WO 02/11794 | 2/2002 |
| 2010/0137827 A1 | 6/2010 | Warren et al. | WO | WO 02/064077 | 8/2002 |
| 2010/0204671 A1 | 8/2010 | Kraushaar et al. | WO | WO 02/076540 | 10/2002 |
| 2010/0243099 A1 | 9/2010 | Yodfat | WO | WO 2005/074860 | 8/2005 |
| | | | WO | WO 2006/082350 | 8/2006 |
| | | | WO | WO 2006/083333 | 8/2006 |
| | | | WO | WO 2006/138184 | 12/2006 |
| | | | WO | WO 2008/028305 | 3/2008 |
| | | | WO | WO 2008/115102 | 9/2008 |

FOREIGN PATENT DOCUMENTS

| | | |
|---|---|---|
| DE | 2005519 | 10/1979 |
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |

OTHER PUBLICATIONS

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009. (2 pages).

* cited by examiner

PIERCING MEMBER PROTECTION DEVICE

TECHNICAL FIELD

The present invention relates to a piercing member protection device which comprises a locking arrangement with a deformable bias flange, to prevent the turning of a first cylindrical member with respect to a second cylindrical member, the locking arrangement is altered between a locked position and an unlocked position by deforming the deformable bias flange.

BACKGROUND OF THE INVENTION

A serious problem in connection with drug preparation, drug administration and other similar handling is the risk that medical and pharmacological staff are exposed to drugs or solvents which might escape into the ambient air. This problem is particularly serious when cytotoxins, antiviral drugs, antibiotics and radiopharmaceuticals are concerned. Other hazardous areas may be sample taking, such as samples concerning virus infections or the like. When performing infusions, it is often necessary to inject a drug or other medical substance into the infusion fluid inside an infusion bag or other infusion fluid container. This is often done by means of penetrating a septum or other fluid barrier of an injection port on the infusion bag or on the infusion fluid line with a needle of a syringe filled with the medical fluid in question. However, even before this it may be necessary to transfer the medical fluid from a vial to a syringe and then from the syringe to a secondary container. In each of these steps staff may be exposed to the medical fluid by means of contamination. Such contamination may be vaporized medical fluid or aerosol in the air. The contaminations may contaminate the staff trough their lungs or vaporized medical fluid or aerosol in the air which condensates on the skin to thereafter penetrate the skin of the staff. Some medicaments are even known to penetrate protection gloves and thereby contaminate the staff.

Exposure to contaminations like this may, on a long term basis, give rise to alarmingly high concentrations of medicaments in the blood or the human body of the just mentioned staff. It has been understood that due to the many transferring steps between e.g. vials, syringes, infusion systems etc. the risk for contamination during the actual insertion and retraction of a needle from e.g. a vial has been underestimated and therefore not properly solved.

For this reason, there has been a need of safer systems for handling and administrating drugs and other medical substances. Accordingly, U.S. Pat. No. 4,564,054 (Gustavsson) discloses a fluid transfer device for transferring a substance from one vessel to another vessel while avoiding leakage of liquid and gas contaminants. The disclosed device comprises a first member designed as a hollow sleeve and having a piercing member provided with a passageway. The piercing member is attached to the first member which has a first barrier member at one end just opposite the tip of the piercing member. Thereby, the piercing member can be passed and retracted through the first barrier member which seals one end of the first member. The fluid transfer device further comprises a second member which is attached to or attachable to one of the vessels or to means arranged to communicate therewith. The second member has a second barrier member, and mating connection means arranged on the first and second members for providing a releasable locking of the members with respect to each other. The barrier members are liquid and gas-proof sealing members which seal tightly after penetration and retraction of the piercing member and prevent leakage of liquid as well as gas contaminants. In the connected position of the first and second members, the barrier members are located in such a way with respect to each other that the piercing member can be passed therethrough.

Similarly, U.S. Pat. No. 4,576,211 discloses a fluid transfer device to which one end a syringe may be connected and to the other end a mouth or opening of a bottle containing a drug or medicine may be connected. The device comprises a closed chamber having enclosed therein a needle which is in connection with the syringe. Connection members are provided by means of which the mouth or opening of the bottle is steadily connected to the device and means enabling the needle to perforate a seal plug and a small rubber plug mounted on the bottle only when the device is locked onto the bottle so that in any case it cannot be disconnected therefrom. The device can be disconnected from the bottle only after the needle has been caused to reenter the closed chamber, so as to prevent any possible dripping of the liquid outside of the device. In order to enable the needle to perforate the seal plug, i.e. to move forward, a rotational movement is required. The connection mechanism uses teeth members which slide in helicoidally elongated slits. The device described in U.S. Pat. No. 4,576,211 is therefore not very user friendly since protection gloves may get caught between the teeth members and the slits during this rotational movement. Furthermore, the solution permits exposure of the needle when the device is not coupled to a vial.

U.S. Pat. No. 3,390,677 discloses a device for transfusion of blood which utilizes a lock system that enables the exposure of the needle in a first position, and an unexposed position of the needle, at a second position. The devices mentioned above have a major drawback in terms of that they can be toggled between the first and the second position independently of whether the device is attached to a vial or not. This has the implication that the needle may be exposed e.g. after blood transfusion has been made, or after the needle has been exposed to cytotoxins, and may thereby be a potential risk. Hence, there are still needs for safer piercing member protection devices.

SUMMARY OF THE INVENTION

The above mentioned drawbacks are at least partly solved by a piercing member protection device as described herein. The piercing member protection device comprises a longitudinal centre axis A, a first cylindrical member with a first and a second end, and an inner and outer surface. The first cylindrical member is at least partly encompassed by a second cylindrical member having a first and a second end, and an inner and outer surface. The second cylindrical member is in turn at least partly encompassed by a third cylindrical member having a first and a second end, and an inner and outer surface. Connection means for connection to a first connection port is further arranged to the first cylindrical member. A piercing member comprising a piercing tip, extends along the longitudinal centre axis A and is directly or indirectly attached to the third cylindrical member, wherein the first cylindrical member comprises a protection chamber to protect at least the piercing tip of the piercing member. The piercing member and the piercing tip is further movable between a secured position in which the piercing tip is enclosed by the protection chamber, so as to prevent the piercing tip of the piercing member from exposure, and an unsecured position, in which the piercing tip of the piercing member is exposed outside the protection chamber and the first cylindrical member. The third cylindrical member is further arranged to turn with respect to the second member between a locked position and an unlocked position, so that when the third cylindrical member is in the locked position, the piercing member is substantially unable to move along the longitudinal centre axis A and when the third cylindrical member is in the unlocked position, the piercing member is enabled to move along the longitudinal centre axis A.

The piercing member protection device further comprises a first locking arrangement which comprises at least one deformable bias flange. The first locking arrangement has a locked position and an unlocked position, wherein when the first locking arrangement is in the locked position, the first cylindrical member is prevented from turning with respect to the second cylindrical member, and when the first locking arrangement is in the unlocked position, the first cylindrical member is permitted to turn with respect to the second cylindrical member. The locked position is altered to the unlocked position by deforming the deformable bias flange by bringing the piercing member protection device in contact with the first connection port. To change to the locked position, the piercing member protection device is removed from contact with the first connection port so as to permit the deformable bias flange to bias back from the deformation to the locked position; this functional relationship will be outlined in greater detail below. The piercing member protection device provides a safe system which prevents a user from accidentally exposing the piercing member before connecting it to a connection port due to the first locking arrangement.

In an embodiment, the first locking arrangement comprises at least one deformable bias flange, preferably two deformable bias flanges. Each of the bias flanges, independently of the number of bias flanges, can be provided with a locking flange adapted to be in working cooperation with a cavity. In this sense, the first locking arrangement can comprise at least one bias flange and at least one cavity. In one embodiment according to the present invention, the at least one deformable bias flange is arranged on the second cylindrical member while the cavity is arranged in the first cylindrical member. This embodiment has been shown to be advantageous from a manufacturing and assembly point of view. Furthermore, the deformable bias flange can be arranged to bias the locking flange towards the first cylindrical member and towards the at least one cavity. The second cylindrical member can further comprise a first and a second deformable bias flange arranged at the first end of the second cylindrical member. As such, when a user pushes the piercing member protection device into, or onto, a connection port, to connect the piercing member protection device, the deformable bias flange(s) is/are deformed to the unlocked position, which permits turning of the first cylindrical member, with respect to the second cylindrical member. Once the first cylindrical member has been turned, with respect to the second cylindrical member, the third cylindrical member can be moved to expose the piercing tip of the piercing member.

In an embodiment, the first and the second deformable bias flanges are connected to the second cylindrical member at a first and a second connection point so that the first and second deformable bias flanges extend between the first and second connection points. Independently of the number of deformable bias flanges, the deformable bias flanges can be attached to the second cylindrical member at the connection points or optionally, which is a preferred solution, the deformable bias flanges are integrated with the second cylindrical member at the connection points, i.e. they are made form the same piece of material. The first and the second deformable bias flanges can further have a substantially crescent-like form which extends between the first and second connection points. Furthermore, a locking flange can protrude out from substantially the centre section of the crescent formed deformable bias flanges. In this latter embodiment of the present invention, the locking flange can be made to protrude into a first connection port before the deformable bias flange is deformed upon contact with the first connection port and thereafter subjected to a deformation force.

In an embodiment, the at least one deformable bias flange is arranged at an angle $\alpha$ with respect to a line transversal to the longitudinal centre axis A, the transversal line being parallel with the first end of the second cylindrical member as shown in FIG. 4c. The angle $\alpha$ is between 10-30°, preferably 23°.

Additionally or optionally, the at least one locking flange can comprise a proximal end, which is connected to the at least one deformable bias flange, and a distal end, intended to be engaged with at least one cavity, when the first locking arrangement is in the locked position. In this embodiment, the distal end of the at least one locking flange has at least one hook element to improve the engagement of the at least one locking flange, with the at least one cavity. The hook element can be arranged to improve the engagement with a cavity arranged in e.g. the first cylindrical member and with respect to the turning motion and as such, improve the locking capabilities of the first locking arrangement.

In an embodiment, the piercing member is arranged to be connected to the third cylindrical member, and the third cylindrical member is arranged to slide along the longitudinal centre axis A, with respect to the second cylindrical member between the secured position and the unsecured position. The piercing member can be arranged to be connected directly or indirectly to the third cylindrical member, e.g. via a fourth member, which e.g. comprises connection means to a second connection port. However the third cylindrical member can comprise connection means to a second connection port, e.g. connection means for connection to a fluid container.

In an advantageous embodiment, the first cylindrical member is connected to the third cylindrical member, so that the first cylindrical member can be turned by means of the third cylindrical member. This can be done by a protrusion and a groove which are arranged in working cooperation. As the first cylindrical member and the third cylindrical member are turned, with respect to the second cylindrical member, the third cylindrical member is positioned so as to be enabled to move along the longitudinal centre axis A, and with respect to the first cylindrical member so as to expose the piercing member or at least the piercing tip of the piercing member.

Furthermore, another aspect of the present invention relates to a piercing member protection device having a longitudinal centre axis A, the piercing member protection device comprises a first cylindrical member with a first and a second end, and an inner and outer surface. The first cylindrical member has a protection chamber for preventing the exposure of at least a piercing tip of a piercing member. The first cylindrical member further comprises a second cylindrical member, with a first and a second end and an inner and outer surface, wherein the first and second end, of the second cylindrical member is arranged between the first and second end, of the first cylindrical member. The first and second cylindrical members are at least partly encompassed by a third cylindrical member. The third cylindrical member comprises a piercing member comprising a piercing tip, and extends along the longitudinal centre axis A. The third cylindrical member is further movable along the longitudinal centre axis A so that the piercing tip of the piercing member can move between an exposed position, at which the piercing tip of the piercing member is exposed outside the protection chamber and an unexposed position, in which piercing tip of the piercing member is inside the protection chamber. The piercing member protection device further has a first and a second locking arrangement. The first locking arrangement is arranged to prevent the first cylindrical member from turning with respect to the second cylindrical member, and the second locking arrangement is arranged to prevent the third cylindrical member from movement long the longitudinal centre axis A. A piercing member protection device as described herein provides for a safe device which effectively prevents a user from accidental exposure to the piercing tip of the piercing member. This in turn reduces the amount of accidents and incidents which could possibly lead to injury.

In an embodiment, the first locking arrangement comprises at least one deformable bias flange comprising a locking flange arranged on the second cylindrical member, the at least one deformable bias flange biases the locking flange towards the first cylindrical member to effectively prevent the first cylindrical member form turning with respect to the second cylindrical member and to thereby keep the first locking arrangement in the locked position. As a user pushes the piercing member protection device into contact with a connection port, the deformable bias flange deforms so as to change the first locking arrangement to the unlocked position. In the unlocked position, the second cylindrical member is held in position by the locking flanges, so that the first cylindrical member can be turned with respect to the second cylindrical member, to thereby put the third cylindrical member in its unlocked position. This in turn permits the movement of the piercing member and the third cylindrical member along the longitudinal centre axis to exposure of the piercing tip of the piercing member.

BRIEF DESCRIPTION OF THE DRAWINGS

The present invention will hereafter be described in greater detail with reference to the accompanying drawings in which.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description.

DETAILED DESCRIPTION OF PREFERRED EMBODIMENTS

Figure 1:
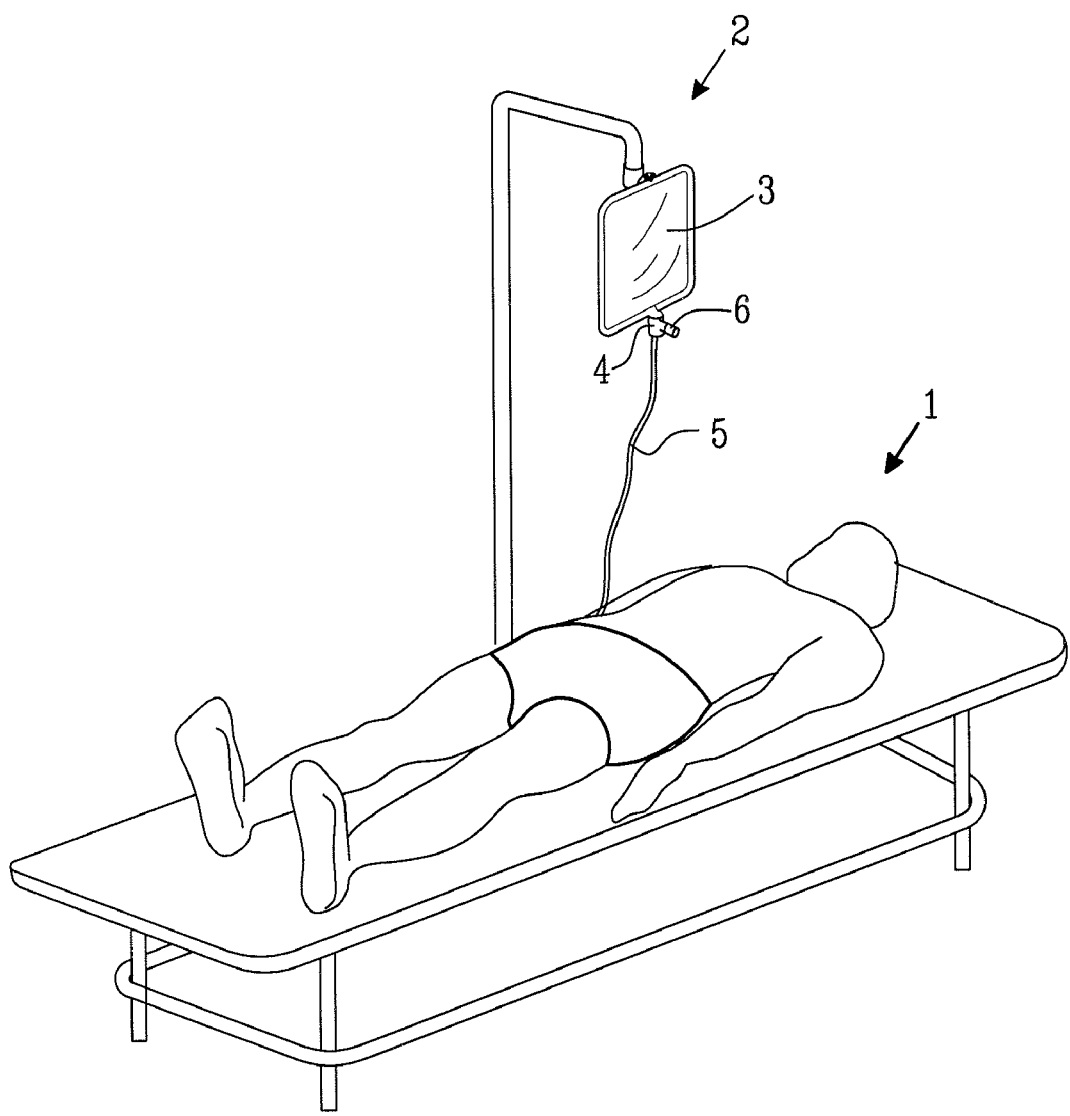
FIG. 1 shows a patient that is administrated with a medicament by an infusion system.

FIG. 1 shows a patient 1 that is being administrated with IV infusion from a medicament administration system 2 comprising a first fluid container 3 provided with a spike infusion device 4. The spike infusion device 4 comprises a fluid channel 5, in fluid communication with the blood circulation system of the patient 1, a piercing member (not shown), forced into the first fluid container 3, and a connection port 6, into which medicine can be administrated by means of a fluid injector device such as a syringe (not shown) connected to a piercing member protection device 9, comprising a piercing member.

Figure 2:
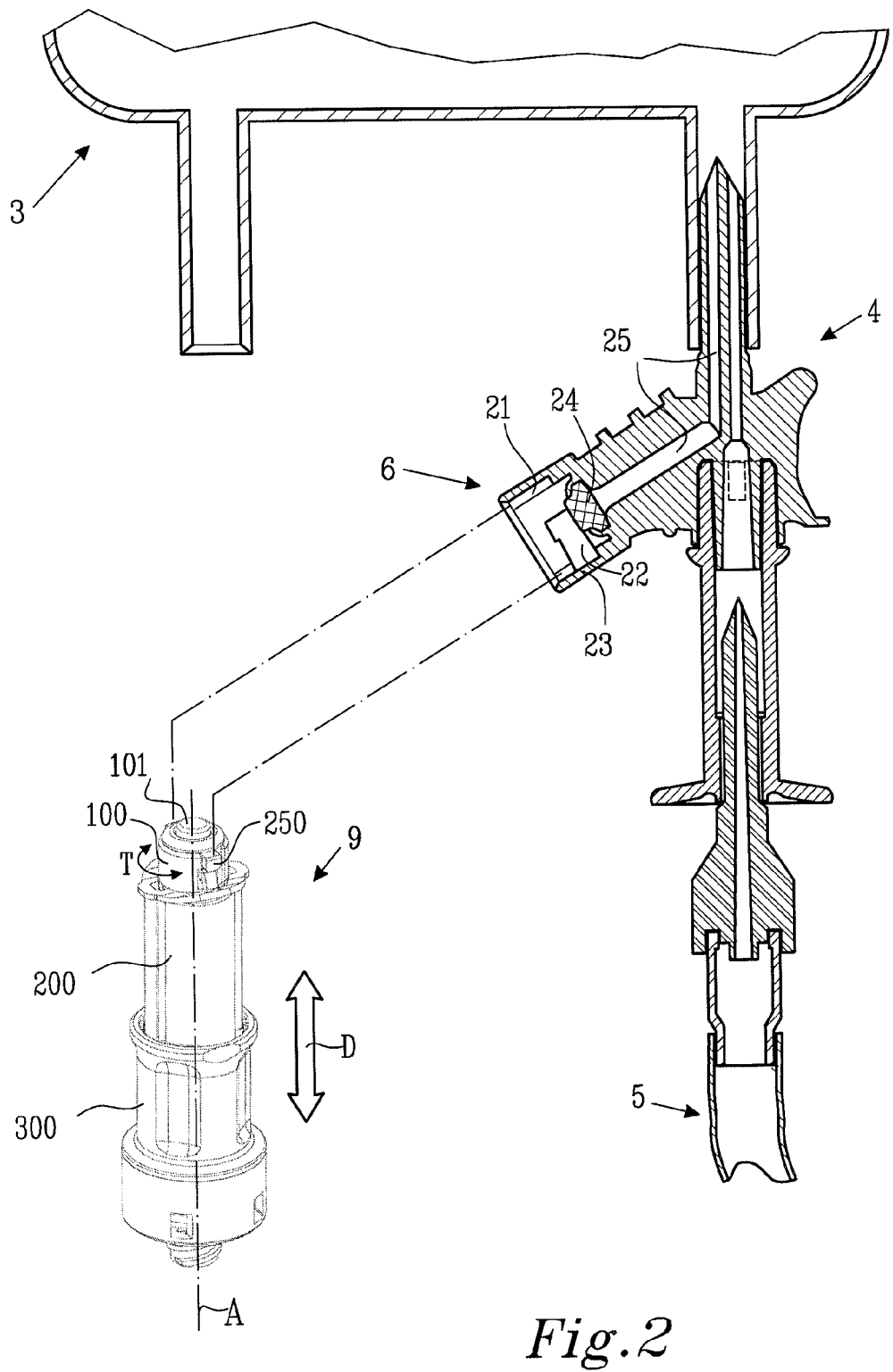
FIG. 2 shows a close up of the infusion system and a piercing member protection device, according to an embodiment.

FIG. 2 shows partly a cross section of a spike infusion device and a connection port 6 to which the piercing member protection device 9 may be connected e.g. during drug administration to the first fluid container 3, although the drug administration to the first fluid container 3 is preferably done before said medicament administration system 2 is connected to a patient. The connection port 6 comprises a first and a second guiding groove 21, 22 arranged on a neck element 23 into which a part of the piercing member protection device 9 can be inserted. A barrier membrane 24 is arranged at the inlet of a fluid channel 25 in fluid communication with the first fluid container 3, so as to provide for a double membrane coupling after connection with the piercing member protection device 9.

The piercing member protection device 9 exhibits a longitudinal centre axis A extending in the longitudinal direction of the piercing member protection device 9 and in the centre of the piercing member protection device 9. The piercing member protection device 9 further comprises a first cylindrical member 100 which is at least partly encompassed by a second cylindrical member 200, which in turn is at least partly encompassed by a third cylindrical member 300. A piercing member (not shown) is connected to the third cylindrical member 300 and extends into a protection chamber defined by the first cylindrical member 100. A first barrier member 101, which after connection with the connection port 6 is intended to provide a double membrane coupling, seals the protection chamber of the first cylindrical member 100 to provide a closed environment for at least the tip of the piercing member of the piercing member protection device 9.

A first locking arrangement 250 is provided between the first cylindrical member 100 and the second cylindrical member 200. The first locking arrangement 250 can be arranged in a first position in which the first cylindrical member 100 is enabled to be turned with respect to the second cylindrical member 200 and a second position in which the first cylindrical member 100 is disabled form turning with respect to the second cylindrical member 200. The second locking device can be alternated between the first and the second position by means of connecting the piercing member protection device 9 to the connection port 6, as will be described in greater detail below.

A second locking arrangement 350 comprises a first position in which the piercing member is enabled to move along the longitudinal centre axis A with respect to the first barrier member 101, and a second position in which the piercing member in disabled to move along the longitudinal centre axis A with respect to the first barrier member 101. The second locking arrangement 350 is alternated between the first position and the second position by means of turning the first cylindrical member 100 with respect to the second cylindrical member 200.

Figure 3:
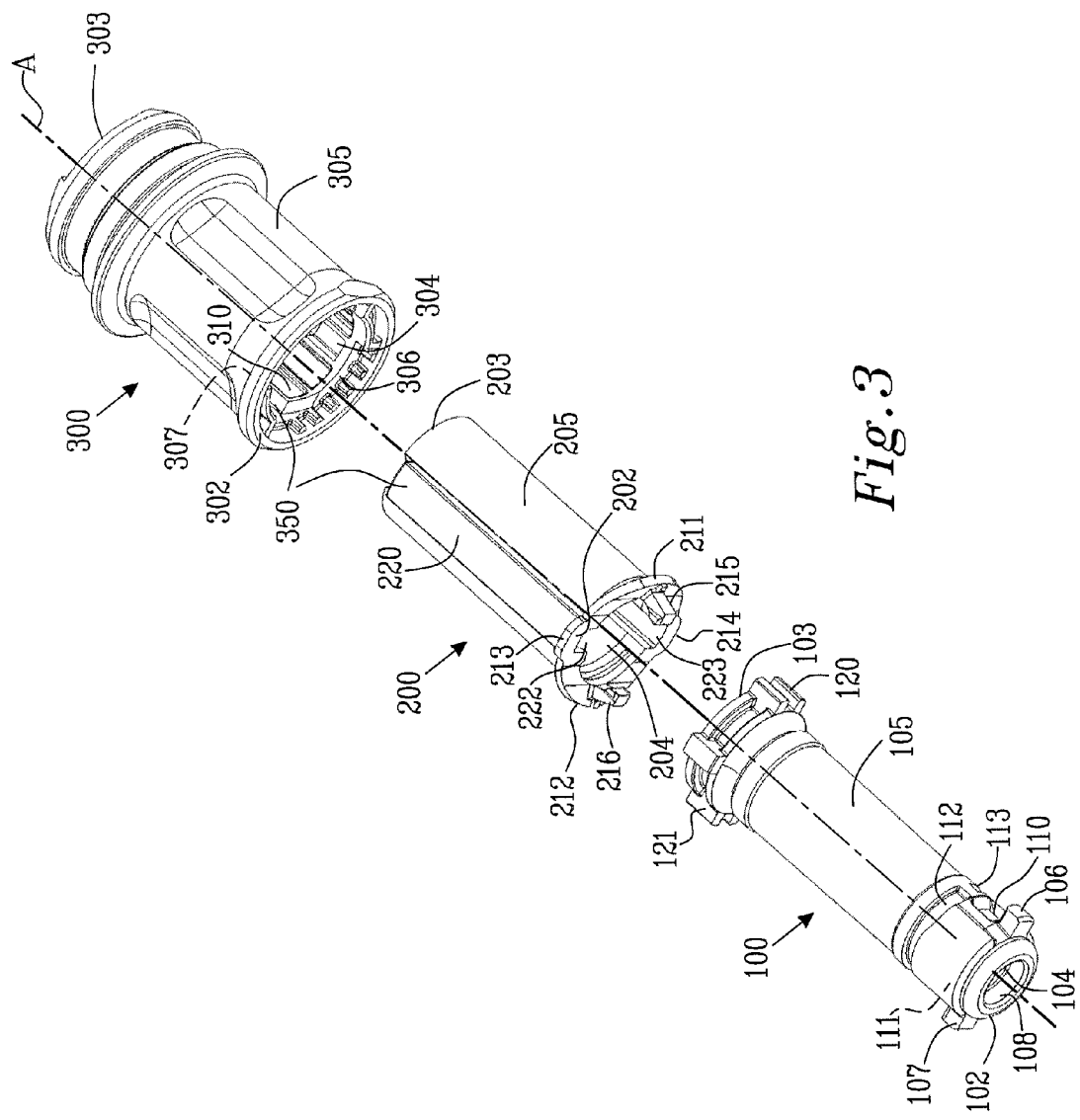
FIG. 3 shows the piercing member protection device as seen in FIG. 2 in an exploded view.

A piercing member protection device according to one embodiment of the present invention is shown in greater detail in FIG. 3 with the first cylindrical member 100, the second cylindrical member 200 and the third cylindrical member 300 in exploded view. As seen in FIG. 3, the first cylindrical member 100 comprises a first and a second end 102, 103 and an inner and an outer surface 104, 105 defining an envelope wall. In the proximity of the first end 102 of the first cylindrical member 100, and protruding out from the outer surface 105 of the first cylindrical member 100 and away from the longitudinal centre line A, is a first and a second protruding locking flange 106, 107 arranged opposite each other. The two protruding locking flanges 106, 107 are intended to, during connection with the connection port 6, be inserted into the two corresponding guiding grooves 21, 22 arranged on the neck element 23 of the connection port 6. The barrier membrane 101 (shown in FIG. 2) is arranged in an opening 108 at the first end 102 of the first cylindrical member 100, to seal the first cylindrical member 100 and the protection chamber therein.

In the proximity of the two protruding locking flanges 106, 107, is a first and a second cavity 110, 111 (although only the first cavity 110 is shown in FIG. 3). More precisely the first and the second cavity 110, 111 and the first and the second protruding locking flange 106, 107 are arranged aligned with the longitudinal centre axis A and on that side of the first and second locking flanges 106, 107 which faces towards the second end 103 of the first cylindrical member 100. During use, the first and the second cavity 110, 111 is intended to receive a locking flange arranged on the second cylindrical member 200, as will be described in greater detail below. The first and second cavities 110, 111 have a substantially rectangular form.

A first and a second transverse locking groove 112, 113 extends in a direction transverse to the longitudinal centre axis A, on the outer surface 105 of the first cylindrical member 100. The first and the second transverse locking groove 112, 113 fixes the second cylindrical member 200 from movement along the longitudinal centre axis A, with respect to the first cylindrical member 100 together with a first and a second snap on protrusion extending from the inner surface of the second cylindrical member 200, while still permitting the first cylindrical member 100 to turn with respect to the second cylindrical member 200, as explained above. During assembly of the first and the second cylindrical member 100, 200, the transverse locking grooves 112, 113 of the first cylindrical member 100, and the first and the second snap on protrusion of the second cylindrical member 200 form a snap on connection.

At the second end 103 of the first cylindrical member 100 is a first and a second turning lock protrusion 120, 121 arranged to lock the third cylindrical member 300 from rotational movement in a direction transverse to the longitudinal centre axis A, i.e. from turning, and with respect to the first cylindrical member 100. As such, the first cylindrical member 100 can always be turned by means of the third cylindrical member 300, with respect to the second cylindrical member 200. The first and the second turning lock protrusions 120, 121 are further arranged to slide in a corresponding groove arranged parallel with the longitudinal centre axis A of the piercing member protection device 9, so as to enable a movement of the third cylindrical member 300 along the longitudinal centre axis A, with respect to the first and second cylindrical members 100, 200. This movement will drive the piercing member from an unexposed position to an exposed position, ready for fluid administration.

The second cylindrical member 200 comprises a first and a second end 202, 203, an inner and an outer surface 204, 205 defining an envelope wall. A deformable locking arrangement 210 is arranged at the first end 202 of the second cylindrical member 200 and comprises a first and a second deformable bias flange 211, 212. Each of the first and second deformable bias flanges 211, 212 are substantially formed as a half circle and are attached to, or preferably form an integral part with, the first end 202 of the second cylindrical member 200 at a first and a second connection point 213, 214. On the first and the second deformable bias flange 211, 212 is a first and a second locking flange 215, 216 arranged to engage the first and the second cavity 110, 111 of the first cylindrical member 100. In this embodiment according to the present invention, the first and second cavities 110, 111 and the first and the second deformable bias flanges 211, 212 together with the first and the second locking flange 215, 216 form the first locking arrangement. As the first and second locking flanges 215, 216 are engaged with the first and the second cavity 110, 111, the first cylindrical member 100 is effectively prevented from turning with respect to the second cylindrical member 200 and as they are disengaged, the first cylindrical member 100 is enabled to turn with respect to the second cylindrical member 200. As is noticed, the first and the second locking flanges 215, 216 are slightly tilted towards the longitudinal centre axis A due to the offset of the first and the second deformable bias flanges 211, 212, as will be described in greater detail with reference to FIG. 4.

The second cylindrical member 200 further comprises a first and a second guide rail 220, 221 which extends parallel with the longitudinal direction A of the piercing member protection device 9, on the outer surface 205 of the second cylindrical member 200. On the inner surface 204 of the second cylindrical member 200 corresponding guiding grooves 222, 223 are arranged. In the shown embodiment the first and second guide rails 220, 221 form the first and second guiding grooves 222, 223 of the second cylindrical member 200 by means of a fold like configuration of the wall of the second cylindrical member 200. The first and second guide rails 220, 221 form part of the second locking arrangement 350 together with a first and a second L-shaped groove of the third cylindrical member 300, enabling the third cylindrical member 300 to alternate between the first position and the second position, as described above.

The third cylindrical member 300 comprises a first and a second end 302, 303, and an inner and outer surface 304, 305 defining an envelope wall. On the inner surface is a first and a second L-shaped groove 306, 307 arranged, wherein one part of the first and second L-shaped groove 306, 307 is parallel to the longitudinal centre axis A of the piercing member protection device 9 and the other part is transverse with the longitudinal centre axis A, enabling the third cylindrical member 300 to either slide along the longitudinal centre axis A or optionally to turn in a direction transverse and around the longitudinal centre axis A, with respect to the second cylindrical member 200.

Additionally grooves, in this embodiment, a first and a second turning lock protrusion groove 310, 311 (the second turning lock protrusion groove not shown) extend parallel to the longitudinal centre axis A on the inner surface 304 of the third cylindrical member 300. After assembly they are in working cooperation with the first and the second turning lock protrusions 120, 121 arranged at the second end 103 of the first cylindrical member 100, as mentioned above. This enables a longitudinal motion of the third cylindrical member 300 along the longitudinal centre axis A, while preventing turning of the third cylindrical member 300, with respect to the first cylindrical member.

Figure 4A:
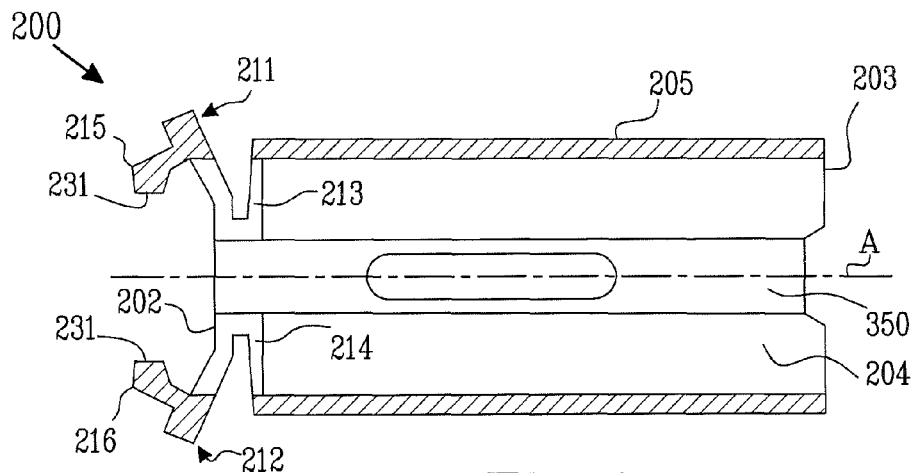
FIGS. 4a-4c show the second cylindrical member, and close ups of the second cylindrical member, of the piercing member protection device, as seen in FIG. 2.

The second cylindrical member 200 will now be described further with reference to FIGS. 4a-4c. FIG. 4a shows a cross section of the second cylindrical member 200 as seen in FIGS. 2 and 3 with the same references used for the same features. As can be seen, the deformable bias flanges 211, 212 extend out from the first and the second connection point 213, 214 at an angle α of about 23° with respect to a direction transverse to the longitudinal centre axis A, as more clearly seen in FIG. 4c. The first and the second connection point 213, 214 is integrated with parts of the first and the second guide rail 220, 221 of the second cylindrical member 200, this provides a supportive function to the first and second deformable bias flanges 211, 212. As can further be seen, the form of the first and second locking flanges 215, 216 is substantially hook like, with a hook like element 231, extending towards the longitudinal centre axis A, arranged to grasp and engage the first and second cavities 110, 111 of the first cylindrical member 100.

Figure 4B:
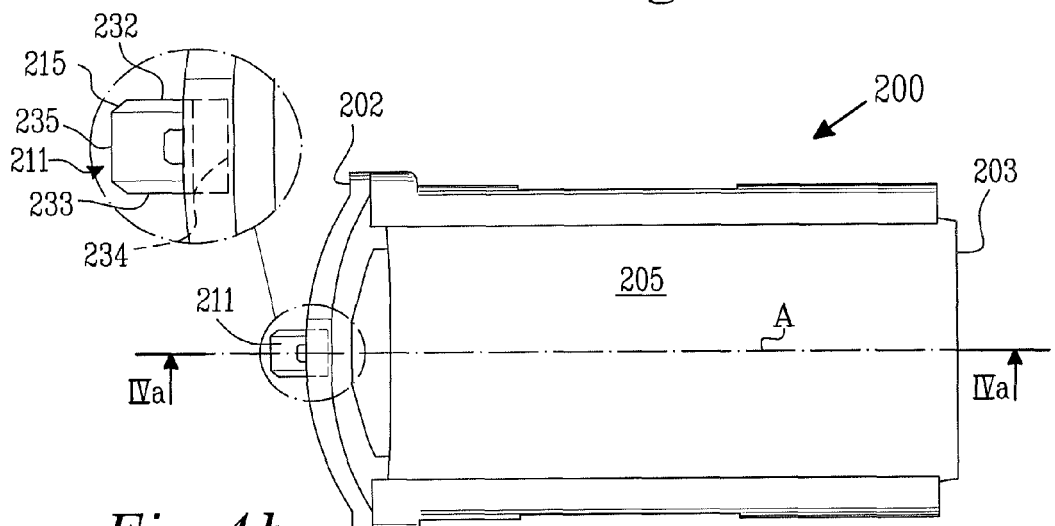
Figure 4C:
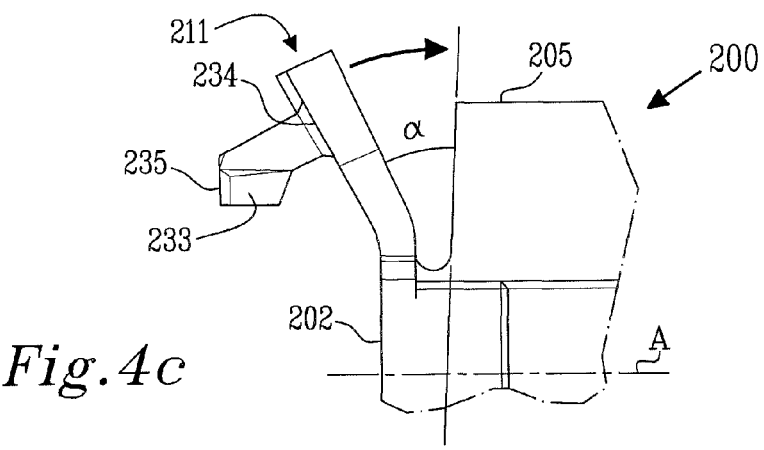

As is further illustrated in FIG. 4b, which shows the second cylindrical member 200 as seen from the side, the first locking flange 215 comprises a proximal end 234, which is arranged on the first deformable bias flange 211, and a distal end 235, which is intended to engage the cavity 110 when the first locking arrangement 250 is in the locked position. At least the distal end 235 comprises additional hook like elements 232, 233 which protrude out from the stem of the first locking flange 215. This is also shown in FIG. 4c from which it is understood that the additional hook like elements 232, 233 will effectively improve the locking capabilities when engaged in the cavity 110 of the first cylindrical member 100 due to the angle formed between the first locking flange 215 and the cavity side wall.

Figure 5:
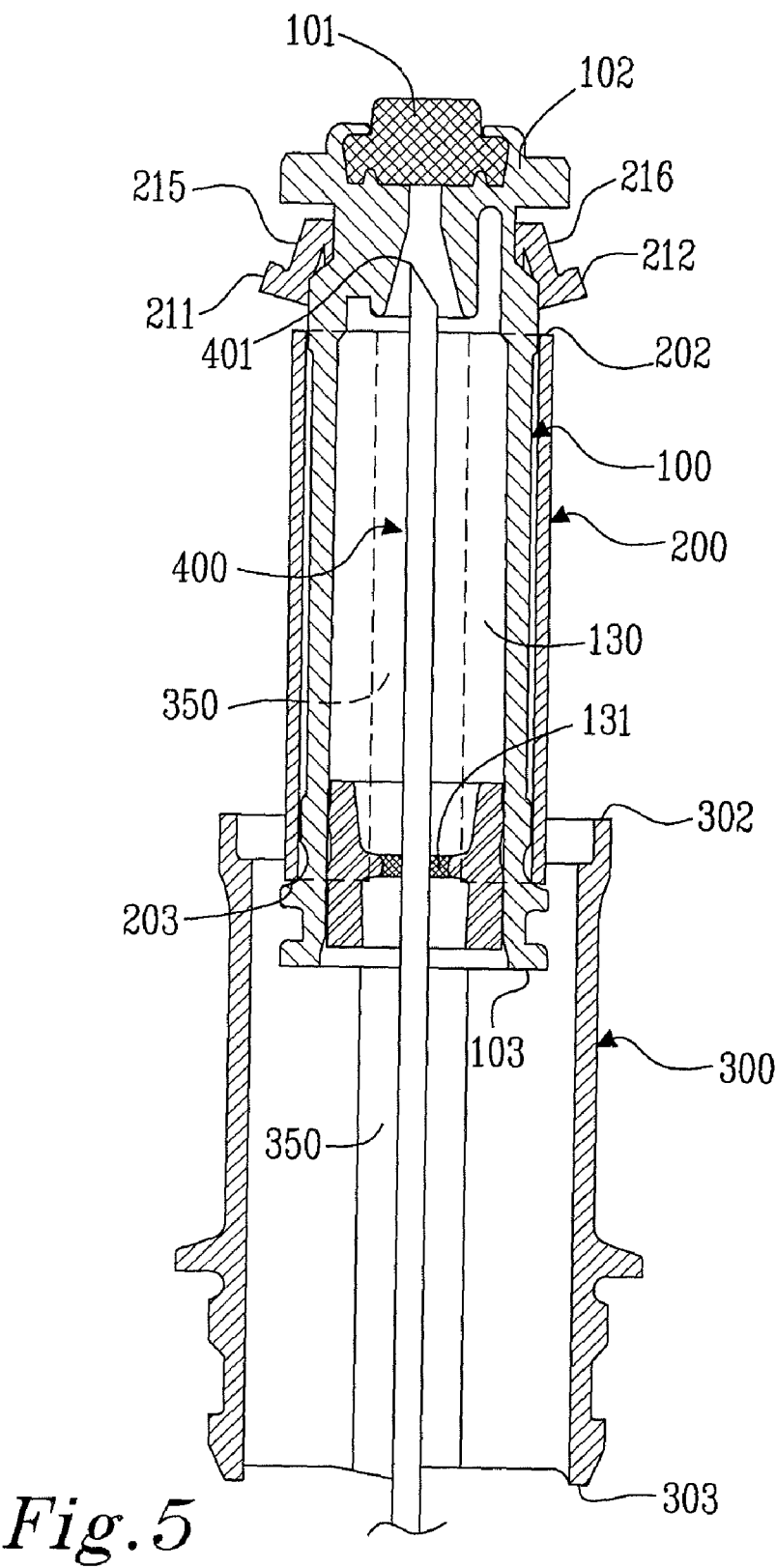
FIG. 5 shows a cross section of parts of the piercing member protection device as seen in FIG. 2.

FIG. 5 shows a cross section of the piercing member protection device 9. Starting from the top, the first cylindrical member 100 comprises a protection chamber 130, i.e. a lumen, which is sealed from the ambient environment by the barrier membrane 101 and optionally a sealing member 131 at the second end 103 of the first cylindrical member 100. The protection chamber 130 which in this embodiment of the present invention, is defined by the envelope wall of the first cylindrical member 100, protects a piercing member 400 and the tip 401 of the piercing member 400 from exposure. By preventing the piercing member 400 from exposure, the risk of accidental injuries or exposure to hazardous medicament is significantly reduced.

The first locking arrangement which is arranged to permit or prevent the first cylindrical member 100 from turning with respect to the second cylindrical member 200 is in the shown embodiment of the present invention a function of, on one side of the first cylindrical member 100, the first deformable bias flange 211 and the first locking flange 215 which are in working cooperation with the first cavity 110 of the first cylindrical member 100, and on the opposite side of the first cylindrical member 100, the second deformable bias flange 212 and the second locking flange 216 which are in working cooperation with the second cavity 111 of the first cylindrical member 100.

As can further be seen, after assembly of the first, second and third cylindrical members 100, 200, 300, the first and second ends 202, 203 of the second cylindrical member 200 are arranged between the first and second ends 102, 103 of the first cylindrical member 100. The first end 302 of the third cylindrical member 300 is arranged between the first end 202 and the second end 203 of the second cylindrical member 200, while both the second end 103 of the first cylindrical member 100 and the second end 203 of the second cylindrical member 200 are arranged between the first and second ends 302, 303 of the third cylindrical member 300. In this sense, the third cylindrical member 300 partly overlap the first and second cylindrical member 100, 200.

Figure 6A:
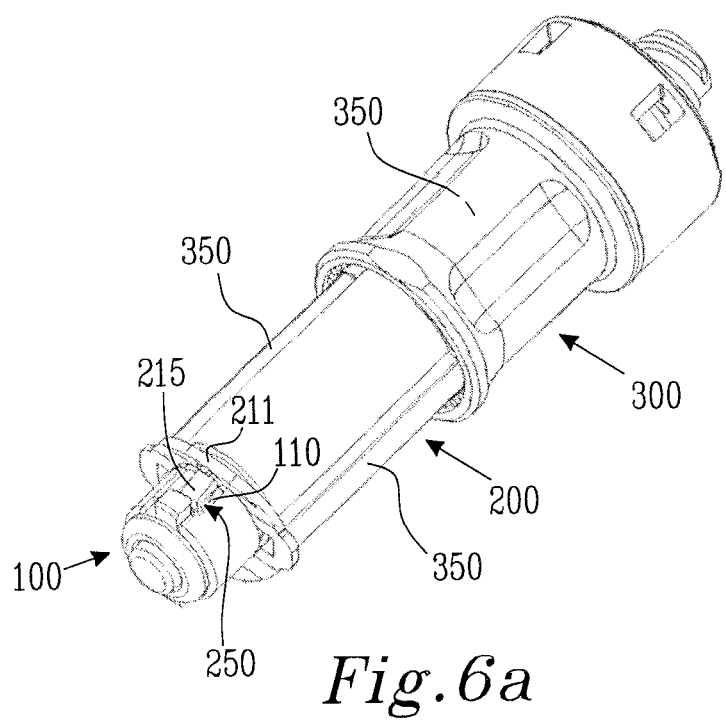
FIGS. 6a-6b show how the first and third cylindrical members are turned with respect to the second cylindrical member.
Figure 6B:
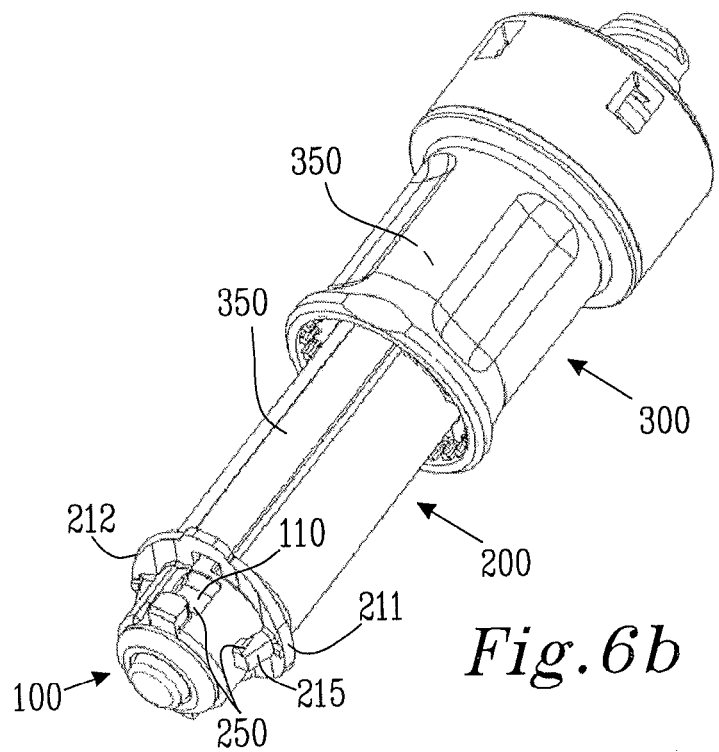

Turning to FIGS. 6a-6b and the function of the piercing member protection device 9, as mentioned, the first and the third cylindrical members 100, 300 can turn with respect to the second cylindrical member 200, as is illustrated in FIGS. 6a-6b. In the shown embodiment, the first cylindrical member 100 is turned approximately 90° with respect to the second cylindrical member 200 to toggle between the locked position, in which the third cylindrical member 300 is unable to move along the longitudinal centre axis A and as seen in FIG. 6a, to the unlocked position, in which the third cylindrical member 300 is able to move along the longitudinal centre axis A. The unlocked position is shown in FIG. 6b. Parts of the first locking arrangement 250, in this embodiment, the first and second deformable bias flanges 211, 212 are, during insertion into the neck element 23, as seen in FIG. 2, deformed and moved along a deformation direction, as indicated by the arrow in FIG. 6a and FIG. 4c. As the deformable bias flanges 211, 212 are deformed, the locking flanges 215, 216 are disengaged from the first and second cavities 110, 111. As they are disengaged, the first cylindrical member 100 can be turned with respect to the second cylindrical member 200 by means of the third cylindrical member 300. Since the first locking arrangement 250 is deformed as the piercing member protection device is inserted into connection port 6, a user never runs the risk of being exposed to the piercing member 400 when the piercing member protection device 9 is not used for its intended purpose.

Figure 7:
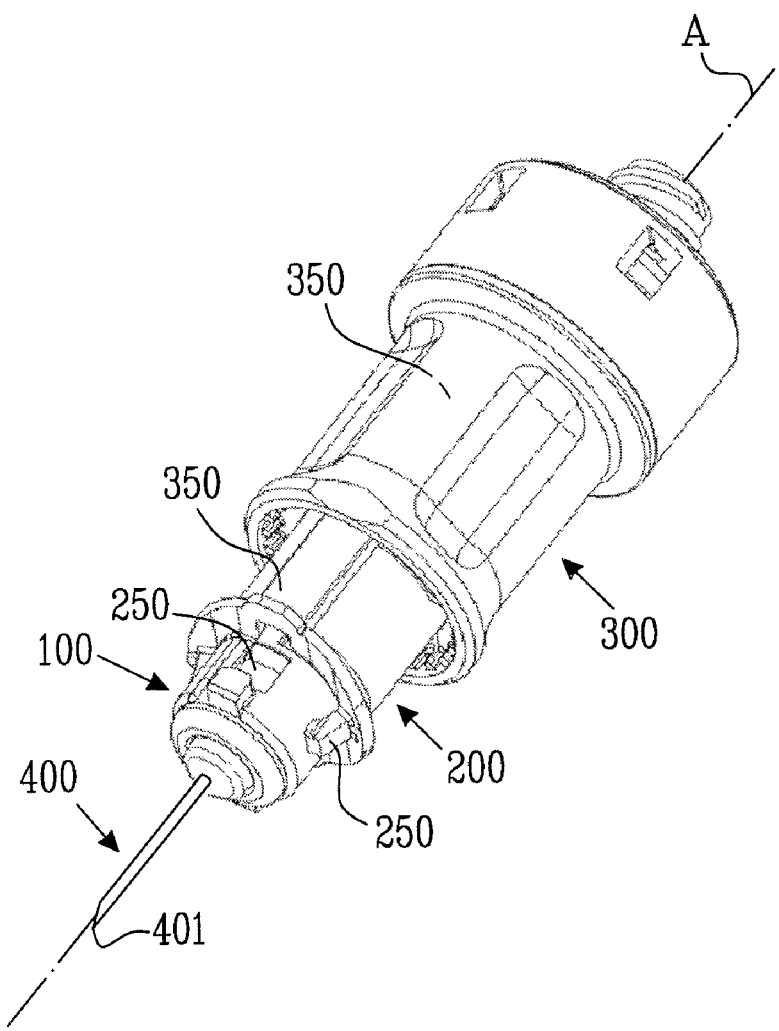
FIG. 7 shows how the piercing tip of the piercing member and the third cylindrical member have been moved with respect to the second cylindrical member and the first cylindrical member along the longitudinal centre axis A.

FIG. 7 shows the piercing member protection device 9 as it would look like after connection with the connection port 6, the first locking arrangement 250 has been disengaged so as to permit the turning if the first and third cylindrical member 100, 300 with respect to the second cylindrical member 200, and the third cylindrical member 300 has been enabled to move along the longitudinal centre axis A and the tip 401 of the piercing member 400 is exposed.

The first, second and third members 100, 200, 300 can comprise any suitable material but preferably comprise or consist of a thermoplastic material such as polypropylene, polyethylene, polyurethane, polystyrene, polyoxymethylene, acrylonitrile-butadienestyrene copolymer (ABS), polyethylene terephthalate or mixtures thereof. The first, second and third members 100, 200, 300 can be made of different material or of the same material but are always separate pieces with respect to each other.

It is to be understood that while the invention has been described in conjunction with the detailed description thereof, the foregoing description is intended to illustrate and not limit the scope of the invention.

The invention claimed is:

1. A piercing member protection device comprising a longitudinal center axis, a first member having a first end and a second end, a second member having a first end and a second end, and a third member having a first end and a second end, wherein
said first member is at least partly encompassed by said second member, and said second member is at least partly encompassed by said third member,
wherein said first member comprises a connection means for connection to a first connection port,
wherein said piercing member protection device is arranged to accommodate a piercing member comprising a piercing tip that extends along said longitudinal center axis and is directly or indirectly attached to said third member, wherein said first member comprises a protection chamber to protect at least said piercing tip of said piercing member, wherein said piercing member and said piercing tip are movable between (i) a secured position in which said piercing tip is enclosed by said protection chamber so as to prevent said piercing tip of said piercing member from exposure and (ii) an unsecured position in which said piercing tip of said piercing member is exposed outside said protection chamber and said first member, wherein said third member is arranged to turn with respect to said second member between a locked position and an unlocked position so that when said third member is in said locked position said piercing member is substantially unable to move along said longitudinal center axis and when said third member is in said unlocked position said piercing member is enabled to move along said longitudinal centre axis, wherein said piercing member protection device comprises a first locking arrangement comprising at least one deformable bias flange, wherein said first locking arrangement has a locked position and an unlocked position, wherein when said first locking arrangement is in said locked position, said first member is prevented from turning with respect to said second member, and when said first locking arrangement is in said unlocked position, said first member is permitted to turn with respect to said second member, and wherein said locked position is arranged to be altered to said unlocked position by deforming said at least one deformable bias flange by bringing said piercing member protection device into contact with said first connection port.

2. The piercing member protection device according to claim 1, wherein said first locking arrangement comprises at least one deformable bias flange provided with a locking flange, and at least one cavity.

3. The piercing member protection device according to claim 2, wherein said at least one deformable bias flange is arranged on said second member, and said cavity is arranged on said first member.

4. The piercing member protection device according to claim 3, wherein said deformable bias flange is arranged to bias said locking flange towards said first member, and when said first locking arrangement is in said locked position, towards said at least one cavity.

5. The piercing member protection device according to claim 4, wherein said second member comprises a first and a second deformable bias flange arranged at said first end of said second member.

6. The piercing member protection device according to claim 5, wherein said first and second deformable bias flanges are connected to said second member at a first and a second connection point, and wherein said first and second deformable bias flanges extend between said first and second connection points.

7. The piercing member protection device according to claim 6, wherein said first and second deformable bias flanges have a substantially crescent-like form which extends between said first and second connection points.

8. The piercing member protection device according to claim 7, wherein said first and second locking flanges protrude out from substantially the center section of said crescent formed first and second deformable bias flanges.

9. The piercing member protection device according to claim 2, wherein said at least one deformable bias flange is arranged at an angle with respect to a line transversal to said longitudinal center axis, said transversal line being parallel with said first end of said second member.

10. The piercing member protection device according to claim 9, wherein said angle is between 10-30°.

11. The piercing member protection device according to claim 2, wherein said at least one locking flange comprises a proximal end that is connected to said at least one deformable bias flange and a distal end that is intended to be engaged with said cavity when said first locking arrangement is in said locked position.

12. The piercing member protection device according to claim 11, wherein said distal end of said at least one locking flange has at least one hook element to improve the engagement of said at least one locking flange with said at least one cavity.

13. The piercing member protection device according to claim 1, wherein said piercing member is arranged to be connected to said third member, and wherein said third member is arranged to slide along said longitudinal center axis, with respect to said second member, between said secured position and said unsecured position.

14. The piercing member protection device according to claim 13, wherein said second end of said third member comprises connection means for connection to a second connection port.

15. The piercing member protection device according to claim 1, wherein said first member is connected to said third member, so that said first member can be turned by means of said third member.

16. The piercing member protection device according to claim 1, wherein said first, said second member, and said third member are cylindrical members.

17. A piercing member protection device comprising a longitudinal center axis, a first member having a first end, a second end, an inner surface, and an outer surface, a second member having a first end, a second end, an inner surface, and an outer surface, and a third member comprising a piercing member that comprises a piercing tip and that extends along said longitudinal center axis, wherein said first member comprises a protection chamber for preventing the exposure of at least said piercing tip of said piercing member, wherein said first end and said second end of said second member are arranged between said first end and said second end of said first member, wherein said first member and said second member are at least partly encompassed by said third member, wherein said third member is movable with respect to said second member and along the longitudinal center axis so that said piercing tip of said piercing member can move between an exposed position, at which said piercing tip is exposed outside said protection chamber, and an unexposed position, in which said piercing tip is inside said protection chamber, wherein said piercing member protection device comprises a first locking arrangement and a second locking arrangement, wherein said first locking arrangement is arranged to prevent said first member from turning with respect to said second member, and wherein said second locking arrangement is capable of being selectively arranged between a locked position and an unlocked position, wherein said locked position is arranged to prevent said third member from movement with respect to said second member and along said longitudinal center axis.

18. The piercing member protection device according to claim 17, wherein said first locking arrangement comprises at least one deformable bias flange comprising a locking flange arranged on said second member, said at least one deformable bias flange biasing said locking flange towards said first member.

19. The piercing member protection device according to claim 17, wherein said first member, said second member, and said third member are cylindrical members.

* * * * *